(12) United States Patent
Walsworth et al.

(10) Patent No.: US 9,784,804 B2
(45) Date of Patent: Oct. 10, 2017

(54) DYNAMIC DECOUPLING IN SOLID STATE SPIN ENSEMBLES

(75) Inventors: Ronald Walsworth, Newton, MA (US); Linh My Pham, Cambridge, MA (US)

(73) Assignee: PRESIDENT AND FELLOWS OF HARVARD COLLEGE, Cambridge, MA (US)

(*) Notice: Subject to any disclaimer, the term of this patent is extended or adjusted under 35 U.S.C. 154(b) by 788 days.

(21) Appl. No.: 14/125,945

(22) PCT Filed: Jun. 13, 2012

(86) PCT No.: PCT/US2012/042232
§ 371 (c)(1),
(2), (4) Date: May 23, 2014

(87) PCT Pub. No.: WO2012/174098
PCT Pub. Date: Dec. 20, 2012

(65) Prior Publication Data
US 2015/0048822 A1    Feb. 19, 2015

Related U.S. Application Data

(60) Provisional application No. 61/496,511, filed on Jun. 13, 2011.

(51) Int. Cl.
*G01V 3/00* (2006.01)
*G01R 33/32* (2006.01)
(Continued)

(52) U.S. Cl.
CPC .......... *G01R 33/323* (2013.01); *G01N 24/08* (2013.01); *G01R 33/60* (2013.01); *G01R 33/24* (2013.01)

(58) Field of Classification Search
CPC .............. G01R 33/543; G01R 33/5659; G01R 33/3415; G01R 33/36; A61B 5/055
(Continued)

(56) References Cited

U.S. PATENT DOCUMENTS 8,138,756 B2 * 3/2012 Barclay ............ B29D 11/00663
324/244.1
8,547,090 B2 * 10/2013 Lukin ................... G01R 33/032
324/244.1
(Continued)

FOREIGN PATENT DOCUMENTS

WO      2009073736 A1    6/2009

OTHER PUBLICATIONS

Pham L M et al: "Magnetic field imaging with nitrogen-vacancy ensembles", New Journal of Physics, Institute of Physics Publishing, Bristol, GB, vol. 13, No. 4, Apr. 28, 2011 (Apr. 28, 2011), p. 45021, XP020189077, ISSN: 1367-2630, DOI: 10.1088/1367-2630/13/4/045021.
(Continued)

*Primary Examiner* — Walter L Lindsay, Jr.
*Assistant Examiner* — Frederick Wenderoth
(74) *Attorney, Agent, or Firm* — Elizabeth Kim Patent Law Offices LLC

(57) ABSTRACT

Long spin coherence lifetimes are realized for ensembles of electronic spin impurities in solid state spin systems, for example NV color centers in diamond, by using spin-control RF pulse sequences to provide dynamic decoupling of the ensembles of spin impurities from environmental sources of decoherence such as dipolar and hyperfine interactions with proximal spin and other paramagnetic impurities in diamond. In this way, the measurement sensitivity of the coherent evolution of ensembles of solid state spin impurities are increased. Using the Carr-Purcell-Meiboom-Gill (CPMG) pulse sequence, the spin coherence lifetimes of NV ensembles can be extended to more than 2 ms in room temperature diamond, and sensitivity of magnetometry that uses NV ensembles can be increased.

24 Claims, 7 Drawing Sheets

(51) Int. Cl.
*G01R 33/60* (2006.01)
*G01N 24/08* (2006.01)
*G01R 33/24* (2006.01)

(58) Field of Classification Search
USPC .................................................... 324/307
See application file for complete search history.

(56) References Cited

U.S. PATENT DOCUMENTS

| | | | |
|---|---|---|---|
| 8,766,630 B2* | 7/2014 | Hollenberg | B82Y 35/00 |
| | | | 324/300 |
| 2010/0308813 A1 | 12/2010 | Lukin et al. | |
| 2011/0062957 A1* | 3/2011 | Fu | G01N 24/088 |
| | | | 324/307 |

OTHER PUBLICATIONS

Taylor J M et al: "High-sensitivity diamond magnetometer with nanoscale resolution", Internet Citation, May 8, 2008 (May 8, 2008), pp. 1-29, XP007908377, Retrieved from the Internet: URL:http://arxiv.org/PS_cache/arxiv/pdf/0805/0805.1367v1.pdf [retrieved on Apr. 28, 2009].

C.A. Ryan et al: "Robust Decoupling Techniques to Extend Quantum Coherence in Diamond", Physical Review Letters, vol. 105, No. 20, Nov. 1, 2010 (Nov. 1, 2010), p. 200402, XP055055329, ISSN: 0031-9007, DOI: 10.1103/PhysRevLett.105.200402.

G. De Lange et al: "Universal Dynamical Decoupling of a Single Solid-State Spin from a Spin Bath", Science, vol. 330, No. 6000, Oct. 1, 2010 (Oct. 1, 2010), pp. 60-63, XP055055327, ISSN: 0036-8075, DOI: 10.1126/science.1192739.

L. T. Hall et al: "Ultrasensitive diamond magnetometry using optimal dynamic decoupling", Physical Review B, vol. 82, No. 4, Jul. 1, 2010 (Jul. 1, 2010), XP055055208, ISSN: 1098-0121, DOI: 10.1103/PhysRevB.82.045208.

J R Maze et al: "Nanoscale magnetic sensing with an individual electronic spin in diamond", Nature, vol. 455, No. 7213, Oct. 2, 2008 (Oct. 2, 2008), pp. 644-647, XP055036129, ISSN: 0028-0836, DOI: 10.1038/nature07279.

W. Witzel et al: "Concatenated dynamical decoupling in a solid-state spin bath", Physical Review B, vol. 76, No. 24, Dec. 1, 2007 (Dec. 1, 2007), XP055055210, ISSN: 1098-0121, DOI: 10.1103/PhysRevB.76.241303.

"International Search Report" for PCT/US2012/.042232, 5 pages, European Patent Office, Rijswijk, The Netherlands, Mar. 14, 2013.

* cited by examiner

DYNAMIC DECOUPLING IN SOLID STATE SPIN ENSEMBLES

CROSS-REFERENCE TO RELATED APPLICATIONS

This application is a 35 U.S.C. §371 National Phase Entry Application of International Application no. PCT/US12/42232 filed Jun. 13, 2012, which designates the U.S., and which claims the benefit of priority under 35 U.S.C §119(e) of U.S. Provisional Patent Application No. 61/496,511 (the "'511 provisional application"), filed Jun. 13, 2011 and entitled "Dynamic Decoupling of Spin Ensembles in Solid State Magnetometry." The contents of each of these applications are incorporated herein by reference in their entireties.

STATEMENT REGARDING FEDERALLY SPONSORED RESEARCH

This invention was made with government support under contract number 60NANB10D002 awarded by NEST (National Institute Of Standards And Technology). The government has certain rights in the invention.

BACKGROUND

The negatively-charged nitrogen-vacancy (NV) color center in diamond possesses many useful properties, including without limitation: long electronic spin coherence times at room temperature; optical mechanisms for initializing and detecting their spin states; and electron spin resonance (ESR) techniques that allow for coherent spin manipulation. The NV color center has generated much interest for scalable applications in quantum information and metrology, such as sensitive detection of electric and magnetic fields.

Dynamical decoupling techniques have been used to reduce the effective interaction of single NV spins with other spin impurities in the environment, enabling significant improvements in the NV single-spin coherence lifetime.

For multi-spin systems, for example ensembles of NV color centers in diamond containing large densities of NV spins, realizing long spin coherence lifetimes remains a challenge. Likewise, there is a need for increasing the sensitivity of magnetometry and other multi-spin metrology that involves ensembles of NVs or other spin impurities.

BRIEF DESCRIPTION OF THE DRAWINGS

The drawings disclose illustrative embodiments. They do not set forth all embodiments. Other embodiments may be used in addition or instead.

DESCRIPTION

Illustrative embodiments are discussed in this disclosure. Other embodiments may be used in addition or instead.

Before the present invention is described in further detail, it should be understood that the invention is not limited to the particular embodiments described, as such may vary. It should also be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, a limited number of the exemplary methods and materials are described herein.

In the present disclosure, methods and systems are described relating to the use of multi-pulse dynamical decoupling to increase the coherence lifetime ($T_2$) of large numbers of spin impurities in solid state spin systems, including without limitation NV electronic spins in room temperature diamond.

Figure 1:
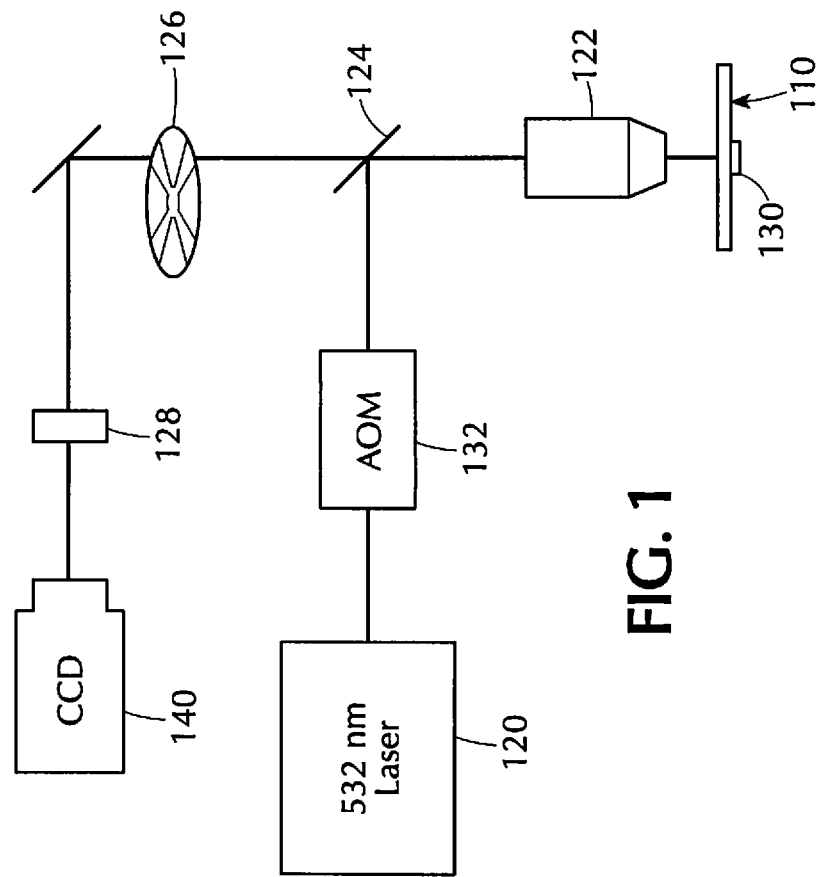
FIG. 1 is a schematic block diagram of a system for implementing multi-pulse dynamical decoupling of an ensemble of NV centers in diamond.

FIG. 1 is a schematic block diagram of a system 100 for implementing multi-pulse dynamical decoupling of solid-state multi-spin systems, which in the illustrated embodiment is an ensemble of NV centers in room temperature diamond. In other embodiments, multi-pulse dynamical decoupling may be performed on solid-state multi-spin systems other than NV centers in diamond, including without limitation phosphorous donors in silicon.

In the illustrated embodiment, the system 100 is a wide-field fluorescence microscope. The system 100 includes a pulsed microwave source 130 configured to generate a series of microwave control pulses and apply them to a sample 110. In the illustrated embodiment, the microwave source 130 is a loop antenna designed to generate a homogeneous $B_1$ field over the sample detection volume, thereby generating resonant microwave control pulses for coherent manipulation of the NV spin states.

In the illustrated embodiment, the sample 110 is a diamond crystal containing an ensemble of NV centers. The spin-bath environment comprises $^{13}$C (carbon 13) nuclear spin impurities and N (nitrogen atom) electronic spin impurities. The diamond samples may consist of an NV-rich layer grown by chemical vapor deposition on a non-fluorescing diamond substrate. In some embodiments, the sample 100 may include an ensemble of spin impurities having a density of at least about $10^2/cm^3$.

The system 100 further includes an optical source 120 configured to generate optical excitation radiation that prepares the NV centers into $m_s=0$ ground states and drives spin-dependent fluorescence detection from the NV centers. In the illustrated embodiment, the optical source 120 is a switched 3-Watt 532-nm laser that can provide optical excitation of NV centers within a 10 μm-diameter cross-section of each sample. An AOM (acousto-optic modulator) 132, for example an Isomet M1133-aQ80 L-H, pulses the excitation laser 120 with precise timing in order to prepare and read out the NV spin states.

The system 100 further includes a detector 140 configured to detect output optical radiation from the spin impurities after being exposed to the optical excitation signal and the series of microwave control pulses. The detector 140 may be an optical fluorescence detector, for example. Many other types of detectors may be used, including without limitation CCD (charge coupled device) arrays and photodiodes.

NV spin state-dependent fluorescence is collected by a microscope objective 122, and is imaged onto the optical fluorescence detector 140 after being separated from the excitation beam by a dichroic mirror 124 and filtered by red filters 128. An optical chopper 126 is synched such that the initialization pulse is blocked from the detector 140, while the readout pulse is recorded. The optical signal is shuttered by the optical chopper 126, allowing spatially resolved ensemble measurements.

A processing system may be integrated with the system 100 described in FIG. 1. The processing system is configured to implement the methods, systems, and algorithms described in the present application. The processing system may include, or may consist of, any type of microprocessor, nanoprocessor, microchip, or nanochip. The processing system may be selectively configured and/or activated by a computer program stored therein. It may include a computer-usable medium in which such a computer program may be stored, to implement the methods and systems described above. The computer-usable medium may have stored therein computer-usable instructions for the processing system. The methods and systems in the present application have not been described with reference to any particular programming language; thus it will be appreciated that a variety of platforms and programming languages may be used to implement the teachings of the present application.

Figure 2A:
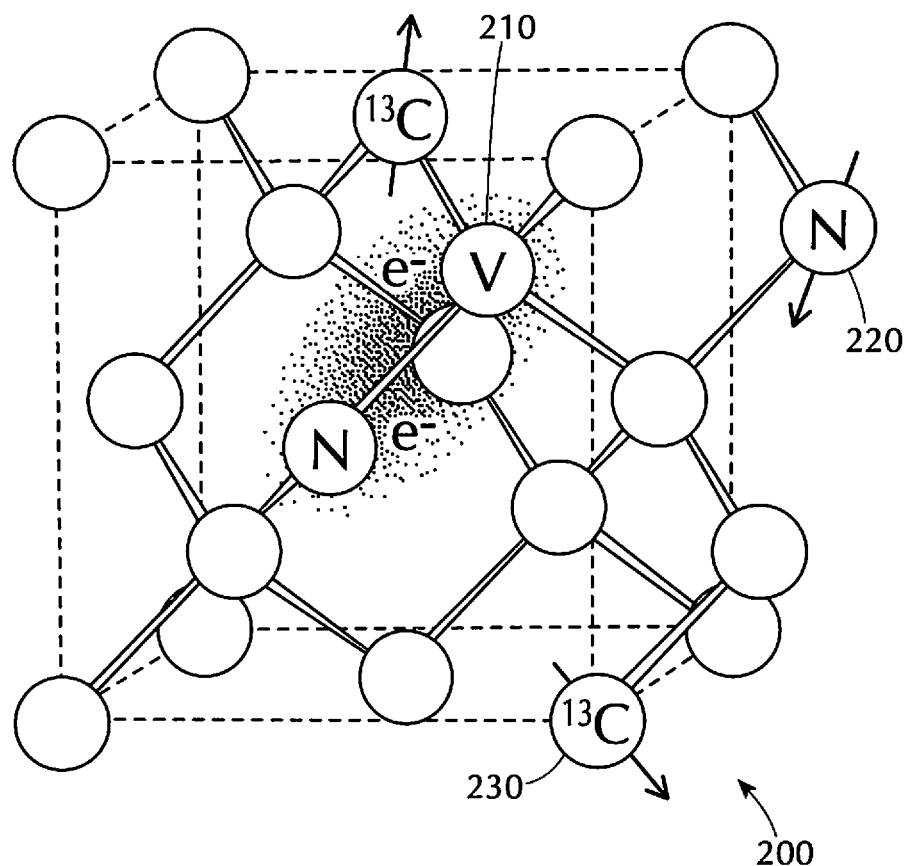
FIG. 2A illustrates an NV color center in a diamond lattice.

FIG. 2A schematically illustrates the crystal structure of an NV center 200 in a diamond lattice. As seen in FIG. 2A, the NV center is an empty position or vacancy resulting from a missing carbon atom in the diamond lattice. The NV impurity is based in the lattice of carbon atoms 210, where two adjacent sites are altered, because one carbon atom is replaced with a nitrogen atom 220 and the other space is left vacant. The vacancies may interact with interstitial atoms such as nitrogen 220, and may act as color centers by absorbing visible light. NV centers are visible as red spots when illuminated by laser. Applying a static field ($B_0$~70 Gauss) along one of the four diamond crystallographic axes selected approximately one quarter of the NV centers to be resonant with the microwave pulses.

Figure 2B:
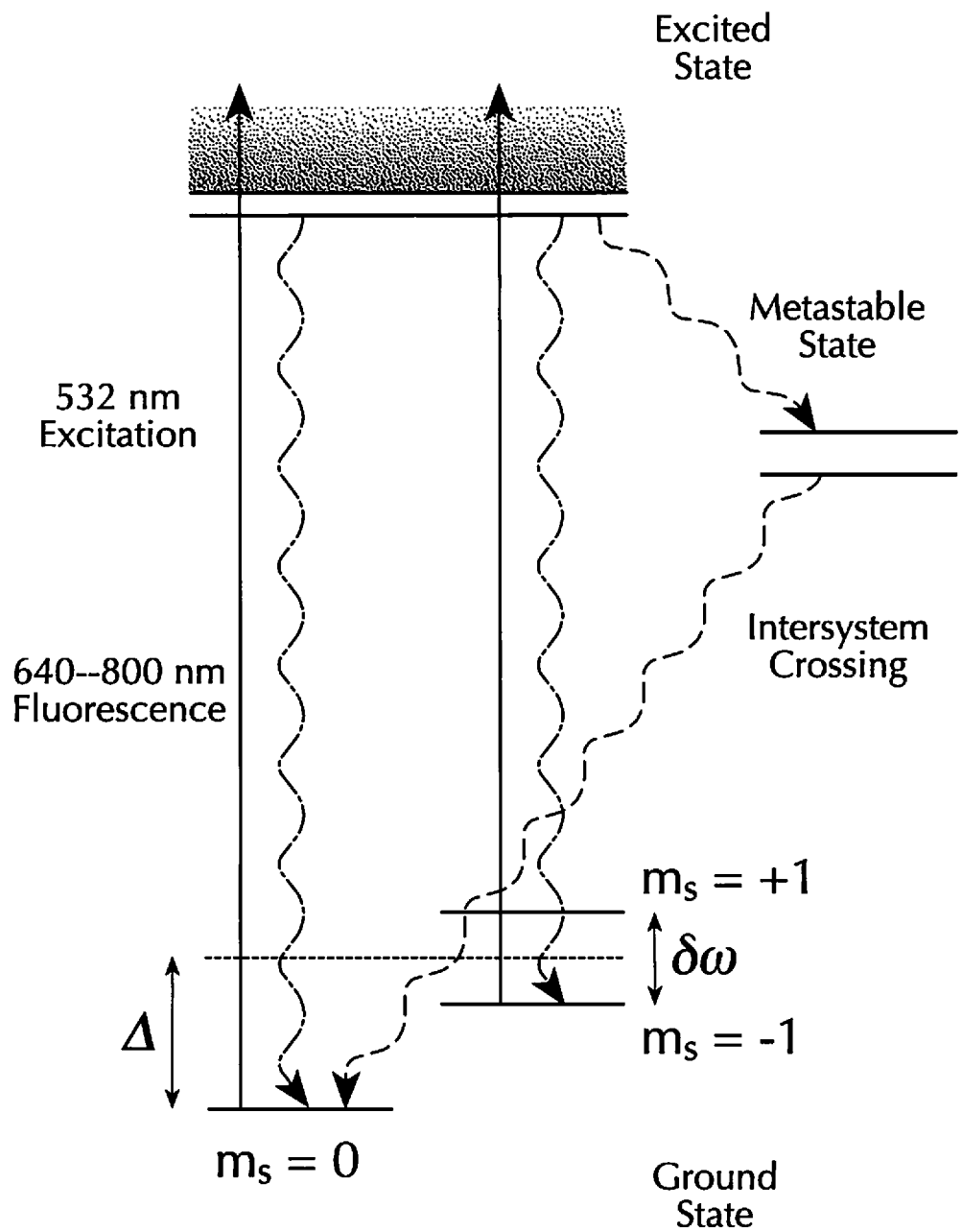
FIG. 2B illustrates the energy level structure of negatively charged NV center shown in FIG. 2A.

FIG. 2B shows the electronic structure of an NV center in diamond. As shown in FIG. 2B, the electronic structure of the negatively charged state of the NV center has a spin-triplet ground state, where the $m_s\pm1$ levels are shifted from the $m_s=0$ level by ~2.87 GHz due to the dipolar spin-spin interaction. Application of an external static magnetic field along the NV axis Zeeman shifts the $m_s\pm1$ levels and allows one to treat the spin manifold as an effective two-level system.

The NV spin environment, i.e., spin bath, is dominated by $^{13}$C and N impurities, randomly distributed in the diamond crystal. These spin impurities create time-varying local magnetic fields at each NV spin, which can be approximated as an average local magnetic field that fluctuates on a timescale set by the mean interaction between spins in the bath, inducing rapid dephasing of freely precessing NV spins on a timescale $T_2^*$~1 μs for typical spin impurity concentrations.

Figure 3:
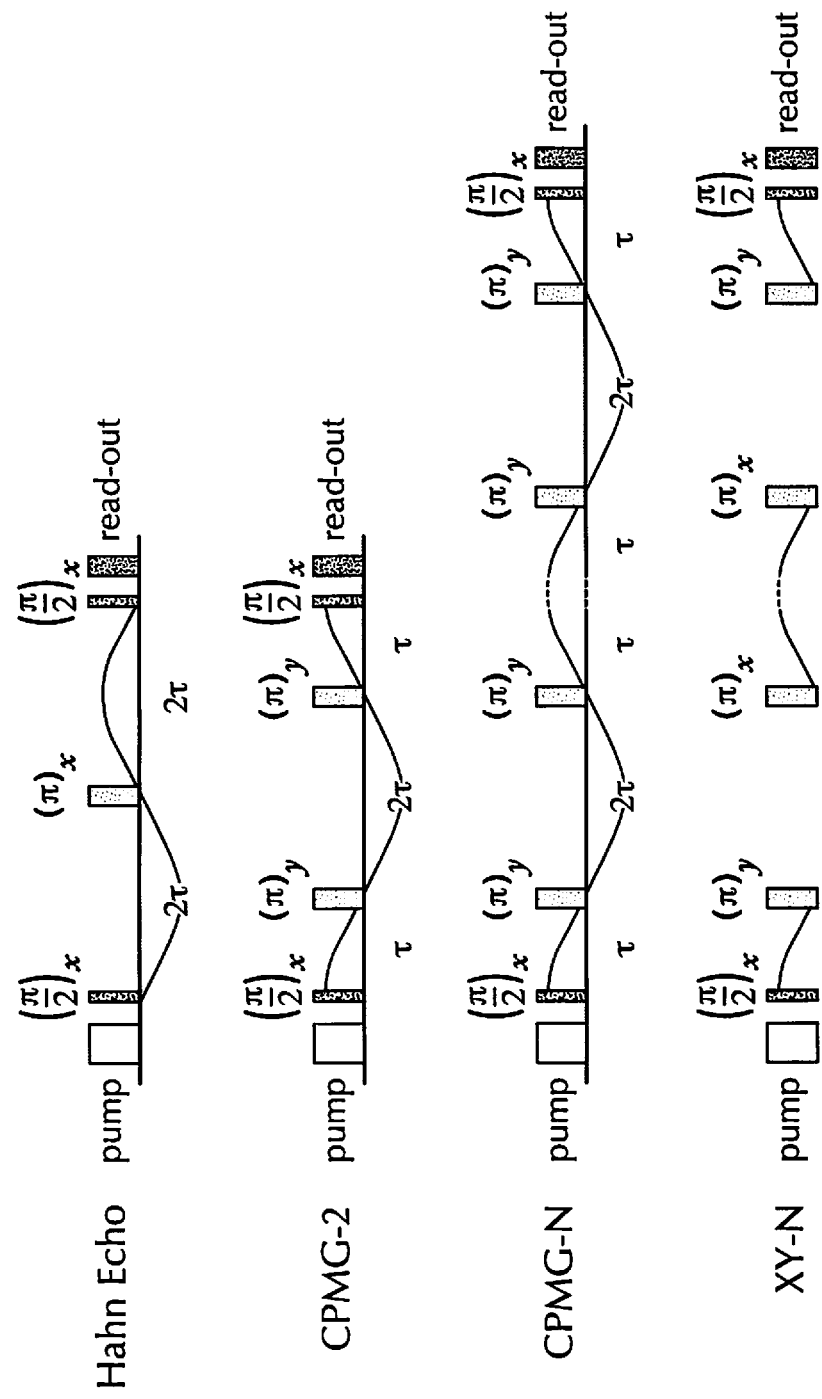
FIG. 3 illustrates a number of different spin control pulses that can be used for dynamic decoupling of multi-spin ensembles, in accordance with some embodiments of the present application.

FIG. 3 illustrates some examples of spin control pulses for dynamic decoupling of multi-spin systems, in one or more embodiments of the present application. An AC magnetic field b(t) is applied, where b(t) has a time dependence represented by:

$$b(t)=b_{ac} \sin [(2\pi\tau_{ac})t+\phi],$$

and the phase φ is chosen such that the nodes of the AC magnetic field b(t) coincide with the microwave π pulses. In particular, the Hahn Echo, CPMG-2, CPMG-N, and XY-N control pulse sequences are shown.

By applying a single resonant microwave π pulse to refocus the dephasing, the Hahn Echo sequence decouples NV spins from bath field fluctuations that are slow compared to the free precession time. Application of additional control pulses, as in n-pulse CPMG (CPMG-N) and n-pulse XY sequences, have been shown to decouple single NV spins from higher frequency bath fluctuations.

In the present application, these additional control pulses are applied to large ensembles of NV spins, resulting in dynamic decoupling of the NV spins from magnetic field fluctuations that are slow compared to the time between the pulses. As discussed below, an order-of-magnitude extension of the coherence lifetime $T_2$ can be realized for diamond samples with widely differing spin environments, using multi-pulse dynamic decoupling.

Figure 4:
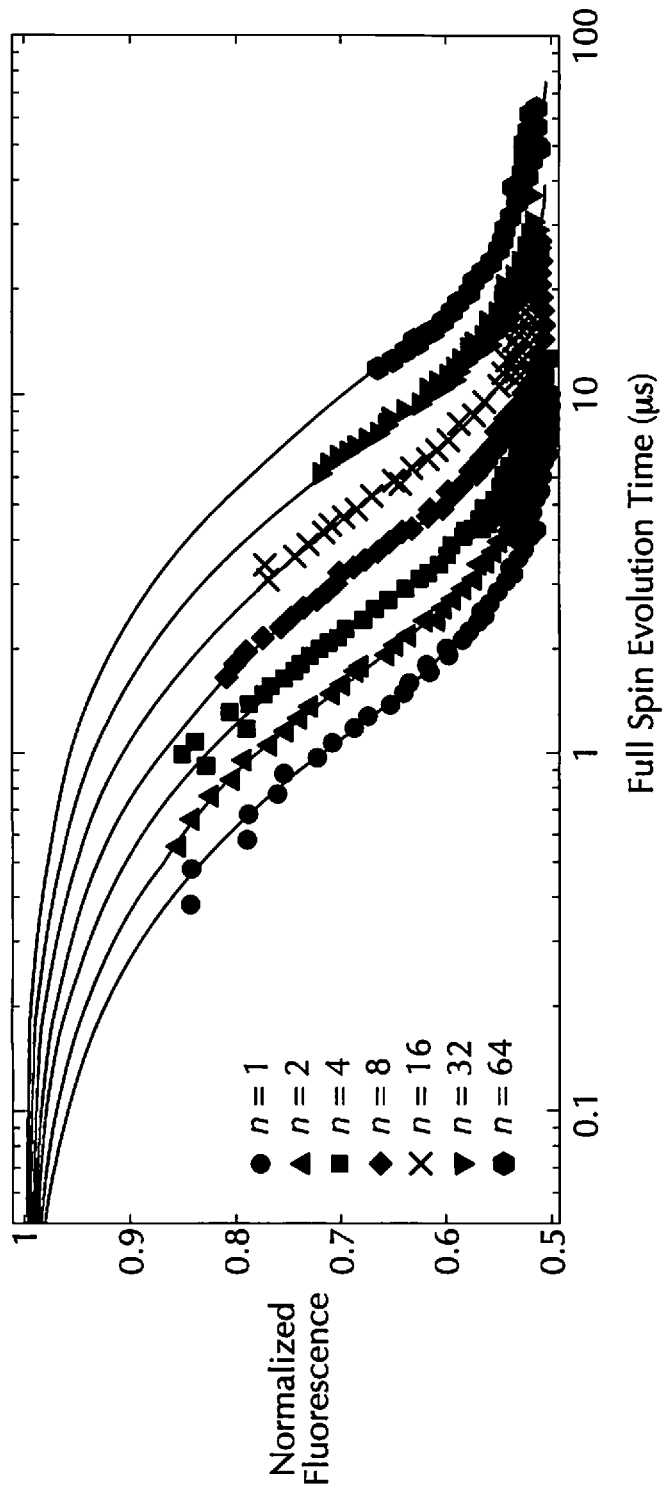
FIG. 4 plots the measurements of NV multi-spin coherent evolution using an n-pulse CPMG control sequence, for a diamond sample having an NV density of ~60 ppb, and a spin-bath environment consisting of 100 ppm nitrogen atoms (N), and 1.1% concentration of $^{13}C$.

FIG. 4 plots the measurements of NV multi-spin coherent evolution using an n-pulse CPMG control sequence, for a diamond sample having an NV density of ~60 ppb (as measured by NV fluorescence intensity), an N concentration of about ~100 ppm (measured by secondary ion mass spectroscopy), and ~1.1% natural abundance $^{13}$C concentration. The high N concentration dominated NV decoherence in this sample, limiting the measured Hahn Echo multi-spin coherence time to $T_2\approx2$ μs.

The diamond sample used in the measurements illustrated in FIG. 4 is an NV-rich layer with a thickness of about 16 μm. CPMG-n sequences were applied to the sample, and the NV multi-spin coherence time was determined as a function of the number of pulses. $T_2^{(n)}$ was determined from the 1/e decay of the spins' coherent evolution as a function of the total CPMG-n evolution period.

The data points in FIG. 4 are representative measurements of NV multi-spin coherence decay for the above-described sample, with $T_2^{(n)}$ extended by a factor >10 for n=128. It was found that $T_2^{(n)}$ exhibited a power-law dependence on n: $T_2^{(n)} \propto n^s$, with s=0.65±0.02 for the sample. These results demonstrate that the inhomogeneities in the spin bath do not limit the effectiveness of dynamical decoupling for extending solid-state multi-spin coherence times by at least an order of magnitude.

When the Hahn echo pulse sequences were applied to two other samples with much lower NV and N concentrations, namely NV~0.2 ppb and N~0.1 ppm for one sample, and NV~0.6 ppb and N~1 ppm for the other sample, similar Hahn Echo NV multi-spin coherence times ($T_2$~300 µs) were measured. By applying n-pulse CPMG dynamical decoupling sequences, the multi-spin $T_2^{(n)}$ was extended to approximately 2 ms (milliseconds) for both samples, which is comparable to the longest coherence time reported for dynamical decoupling applied to single NV centers.

In some embodiments of the present application, dynamical decoupling as described above can be applied to improve the sensitivity of NV multi-spin magnetometry. In a standard AC magnetometry measurement utilizing a Hahn Echo sequence, an oscillating magnetic field, $b(t)=b_{ac} \sin[(2\pi\tau_{ac})t+\phi]$, induces a net phase accumulation of the NV spin coherence, which is maximized when the full time of the Hahn Echo sequence is equivalent to the period of the AC magnetic field ($\tau_{ac}$) and the phase offset $\phi$ is such that the control pulses coincide with nodes in the magnetic field. Under these conditions, the field amplitude $b_{ac}$ can be extracted from the measurement of accumulated NV spin phase with optimum sensitivity, where an approximate expression for the sensitivity is given by:

$$\eta_{HE} \approx \frac{\pi\hbar}{2g\mu_B} \frac{1}{C\sqrt{\tau_{ac}}} \exp\left[\left(\frac{\tau_{ac}}{T_2}\right)^p\right].$$

In the above expression, C is a parameter that encompasses the measurement contrast, optical collection efficiency, and number of NV spins contributing to the measurement. The contrast is modified by NV decoherence over the course of the measurement, described phenomenologically by an exponential factor with power p. The value of p is found to be sample dependent, in the range of 1 to 2.5, and is related to the dynamics of the spin environment and to ensemble inhomogeneous broadening.

In an AC magnetometry measurement utilizing n-pulse dynamical decoupling, the sensitivity is given approximately by the with two modifications: The measurement time is increased by $\tau_{ac} \rightarrow n/2\ \tau_{ac}$, and the NV multi-spin coherence time is extended by $T_2 \rightarrow T_2 n^s$. The resulting sensitivity is given by:

$$\eta_{(n)} \approx \frac{\pi\hbar}{2g\mu_B} \frac{1}{C\sqrt{\frac{n}{2}\tau_{ac}}} \exp\left[\left(\frac{n^{(1-s)}\tau_{ac}}{2T_2}\right)^p\right].$$

Because the measurement time increases linearly with the number of control pulses n, whereas the coherence time increases sub-linearly, there is an optimum number of pulses $n_{opt}$ that yields the most sensitive measurement of an AC magnetic field of period $\tau_{ac}$ given a set of sample-determined parameters:

$$n_{opt} = \left[\frac{1}{2p(1-s)}\left(\frac{2T_2}{\tau_{ac}}\right)^p\right]^{\frac{1}{p(1-p)}}.$$

For a given sample, all the parameters except $\tau_{ac}$ are fixed, so that the above equation can be simplified to: $n_{opt} \alpha (1/\tau_{ac})^{1/p(1-s)}$. Thus, at higher AC frequencies, more pulses are needed to reach the optimum sensitivity. The high frequency regime corresponds to short time intervals between control pulses during which time there is very little contrast lost due to decoherence, i.e. $\tau_{ac}$ is much less than $T_2$. More pulses increase the sensitivity by allowing for a longer measurement time and subsequently more phase accumulation per measurement. Therefore, multi-pulse sequences are more effective at enhancing magnetometry sensitivity in the high-frequency regime, where the Hahn Echo scheme provides relatively poor magnetic field sensitivity.

Figure 5:
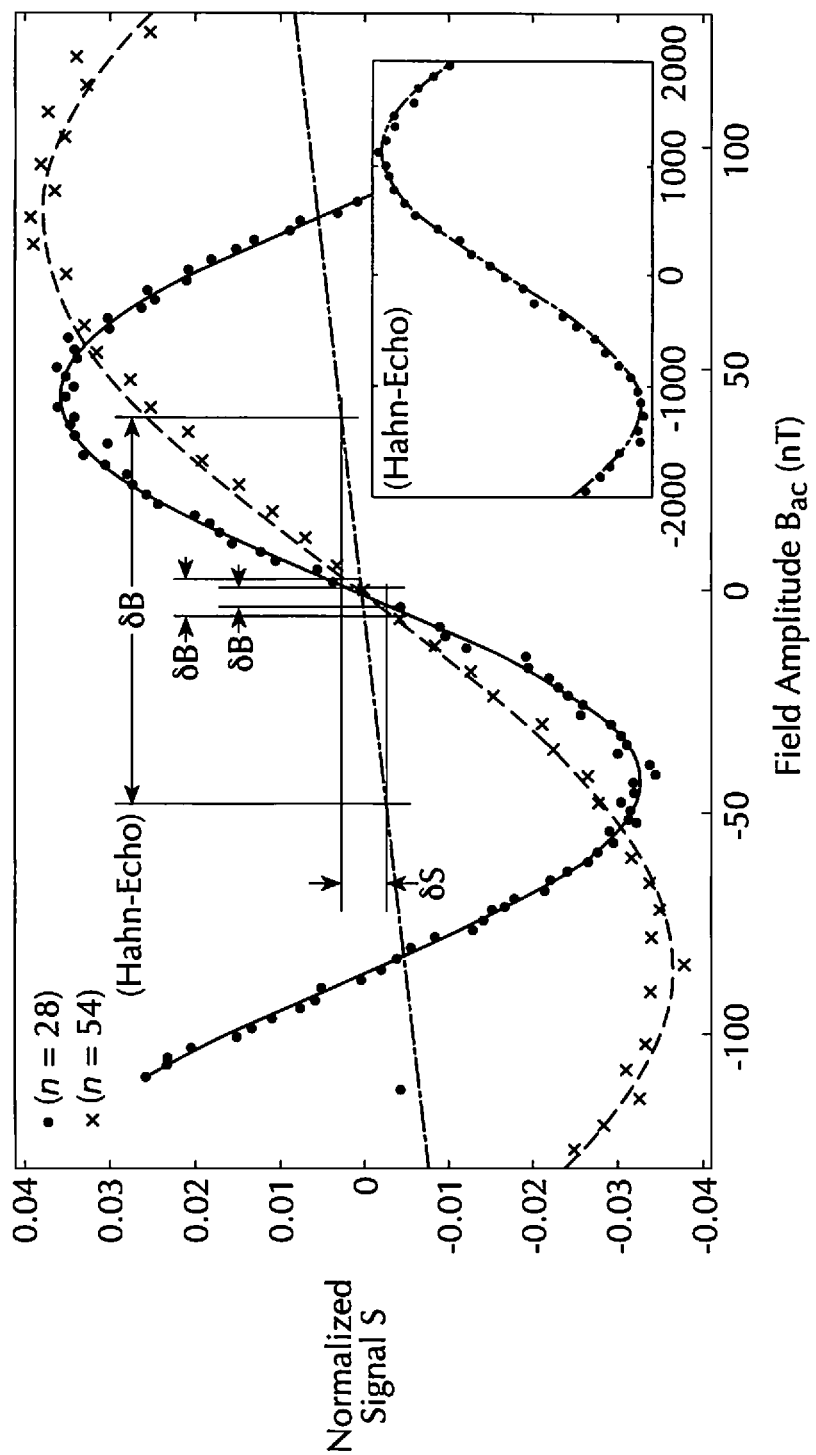
FIG. 5 illustrates examples of measured normalized fluorescence signals as functions of AC field magnitude $B_{ac}$ using a Hahn Echo sequence and multi-pulse XY sequences with different numbers of control pulses.

In one embodiment of the present disclosure, the AC magnetic field sensitivity was measured for a 30 µm³ sensing volume of a diamond sample with NV~0.6 ppb and N~1 ppm, with ~$10^3$ sensing NV spins. FIG. 5 illustrates examples of measured normalized fluorescence signals as functions of AC field magnitude $b_{ac}$ using a Hahn Echo sequence, and using multipulse XY sequences with 28 and 54 control pulses. As seen in FIG. 5, the uncertainty in the measured signal ($\delta S$) limits the uncertainty in the extracted magnetic field magnitude ($\delta B$). The sine behavior of the signal with respect to $b_{ac}$ is achieved by shifting the phase of the last microwave pulse by 90° from what is shown in FIG. 3.

Figure 6:
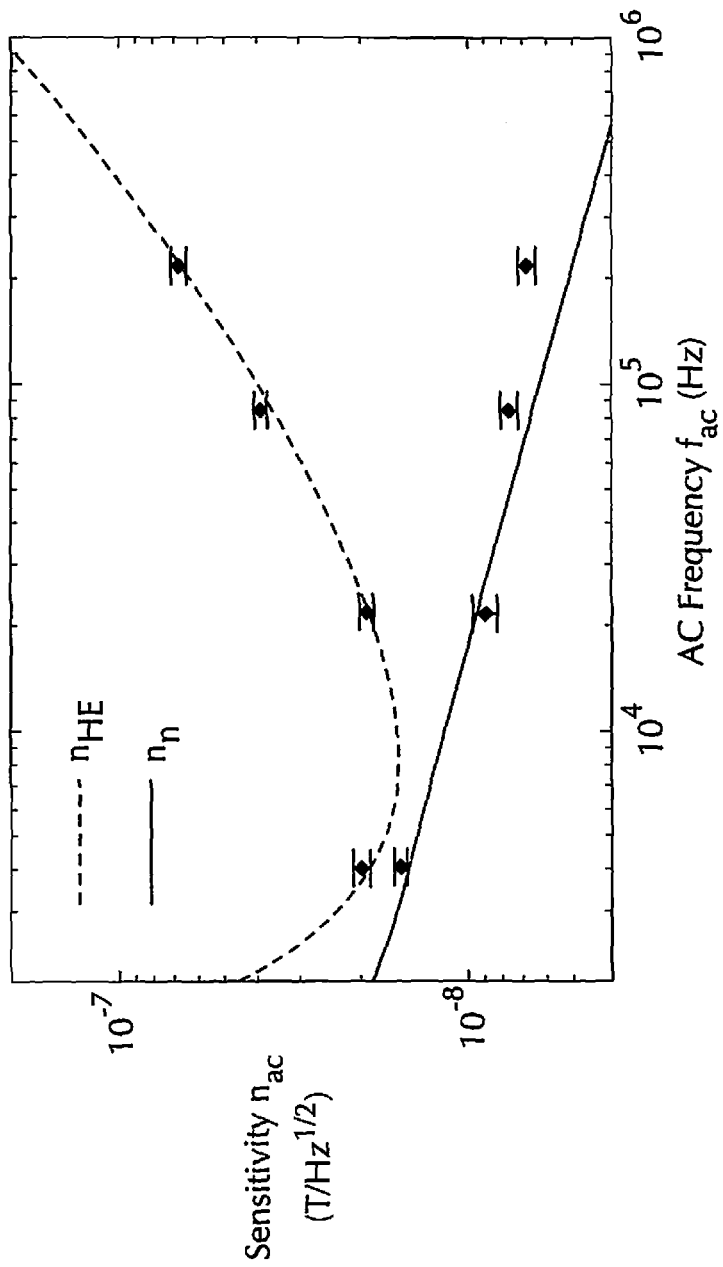
FIG. 6 provides a comparison of calculated and measured AC magnetic field sensitivity, using dynamical decoupling control pulses.

FIG. 6 provides a comparison of calculated (lines) and measured (points) sensitivity, at several AC magnetic field frequencies. As seen in FIG. 6, NV multi-spin measurements confirm that multi-pulse dynamical decoupling outperform the Hahn Echo scheme over a wide range of AC magnetic field frequencies, in agreement with theoretical expectations. The enhancement in magnetic field sensitivity provided by multi-pulse dynamical decoupling is especially pronounced at frequencies higher than the Hahn Echo $1/T_2$ coherence.

In summary, methods and systems have been described for the application of dynamical decoupling to multi-spin systems, in particular large ensembles of NV centers. Multi-pulse dynamical decoupling sequences have been disclosed that can extend the coherence lifetime of large numbers of NV electronic spins in room temperature diamond, by about an order of magnitude, for samples with widely differing NV densities and spin environments.

Using the methods and systems described in the present application, NV multi-spin coherence time greater than about 2 ms can be realized. This is comparable to the best results from application of dynamical decoupling to single NV centers. Multi-pulse dynamical decoupling improves NV multi-spin AC magnetic field sensitivity relative to the Hahn Echo scheme, with about a ten-fold enhancement for higher frequency fields.

Nothing that has been stated or illustrated is intended to cause a dedication of any component, step, feature, object, benefit, advantage, or equivalent to the public. While the specification describes particular embodiments of the present disclosure, those of ordinary skill can devise variations of the present disclosure without departing from the inventive concepts disclosed in the disclosure.

While certain embodiments have been described, it is to be understood that the concepts implicit in these embodiments may be used in other embodiments as well. In the present disclosure, reference to an element in the singular is not intended to mean "one and only one" unless specifically so stated, but rather "one or more." All structural and functional equivalents to the elements of the various embodiments described throughout this disclosure, known or later come to be known to those of ordinary skill in the art, are expressly incorporated herein by reference.

What is claimed is:

1. A method comprising:
   generating periodic microwave pulses using a processing system in a microwave pulse source, and
   applying the periodic microwave pulses to an ensemble of electronic spin impurities in a spin-bath environment of a solid-state spin system, using the processing system;
   wherein the microwave pulses are controlled and sequenced by the processing system in a way that when the microwave pulses are applied to the spin impurities in the presence of an external magnetic field, the spin impurities become decoupled from one or more sources of decoherence in the spin-bath environment to thereby increase coherence times of the spin impurities.

2. The method of claim 1, wherein the solid-state spin system comprises a diamond crystal, wherein the ensemble of electronic spin impurities comprises an ensemble of NV (nitrogen-vacancy) centers in the diamond crystal, and wherein the sources of decoherence comprise a fluctuating magnetic field generated by at least some of the spin impurities.

3. The method of claim 1, wherein the ensemble of spin impurities has a density of at least about $10^{12}/cm^3$.

4. The method of claim 1, wherein the microwave pulses are controlled and sequenced so as to form at least one of:
   a Hahn spin-echo pulse sequence;
   a CPMG (Carr Purcell Meiboom Gill) pulse sequence; and
   a MREVB pulse sequence.

5. The method of claim 1, wherein the external magnetic field is an AC magnetic field having a time dependence b(t) represented by:

$$b(t)=b_{ac} \sin [(2\pi\tau_{ac})t+\phi],$$

and wherein the microwave pulses comprise microwave $\pi$ pulses that coincide with the nodes of b(t).

6. The method of claim 2, further comprising an act of applying optical radiation to the NV centers before applying the microwave pulses, so as to prepare the NV centers into $m_s=0$ ground states, and generate spin-dependent fluorescence signals from the NV center.

7. The method of claim 2, wherein the spin-bath environment comprises $^{13}C$ (carbon 13) nuclear spin impurities and N (nitrogen atom) electronic spin impurities.

8. The method of claim 2, wherein the microwave pulses are controlled and sequenced so as to form at least one of: an XY pulse sequence and a CPMG-n pulse sequence; and wherein the XY pulse sequence and the CPMG-n pulse sequence are configured to decouple single NV spins in the ensemble from higher frequency Pin-bath fluctuations.

9. The method of claim 7, wherein the sources of decoherence in the spin bath environment include fluctuating magnetic fields generated by the $^{13}C$ and N spin impurities, and wherein the magnetic field fluctuations are slow compared to time period between the pulses.

10. The method of claim 6, further comprising an act of detecting a magnetic field by measuring a Zeeman shift in energy levels that the spin impurities undergo in response to the optical radiation and the microwave pulses applied thereto.

11. The method of claim 10, further comprising applying a number $n_{opt}$ of microwave pulses to the spin impurities so as to maximize sensitivity of the magnetic field detection; and wherein $n_{opt}$ is given by:

$$n_{opt} = \left[\frac{1}{2p(1-s)}\left(\frac{2T_2}{\tau_{ac}}\right)^p\right]^{\frac{1}{p(1-p)}}$$

where
$T_2$ represents the multi-spin coherence lifetime of the ensemble of spin impurities;
$\tau_{ac}$ represents the period of the magnetic field being detected;
s is a scaling factor representing scaling of the NV multi-spin coherence times with the number of CPMG pulses, and
p is a phenomenological parameter describing the power of the exponential factor representing NV decoherence over time.

12. A system comprising:
   a pulsed microwave source including a processing system, the processing system configured to generate periodic microwave pulses and apply them to a sample containing an ensemble of electronic spin impurities in a spin-bath environment of a solid-state spin system, the processing system further configured to control and sequence the microwave pulses so that, when applied to the sample in the presence of an external magnetic field, the spin impurities become decoupled from one or more sources of decoherence in the spin-bath environment to thereby increase coherence times of the spin impurities.

13. The system of claim 12, wherein the solid-state spin system comprises a diamond crystal, and wherein the ensemble of electronic spin impurities comprise an ensemble of NV centers in the diamond crystal.

14. The system of claim 12, wherein the ensemble of electronic spin impurities has a density of at least about $10^{12}/cm^3$.

15. The system of claim 12, wherein the microwave pulses are sequenced so as to form at least one of:
   a Hahn spin-echo pulse sequence;
   a CPMG (Carr Purcell Meiboom Gill) pulse sequence; and
   a MREVB pulse sequence.

16. The system of claim 12, further comprising a sample containing the ensemble of electronic spin impurities in the spin-bath environment of the solid-state spin system.

17. The system of claim 12, wherein the microwave source comprises a loop antenna.

18. The system of claim 12, wherein the external magnetic field is an AC magnetic field having a time dependence b(t) represented by:

$$b(t)=b_{ac} \sin [(2\pi\tau_{ac})t+\phi],$$

and wherein the periodic microwave pulses comprise microwave $\pi$ pulses that coincide with the nodes of b(t).

19. The system of claim 13, wherein the spin-bath environment comprises $^{13}C$ nuclear spin impurities and N electronic spin impurities.

20. The system of claim 13, wherein the microwave pulses are sequenced so as to form at least one of:
   an XY pulse sequence and a CPMG-n pulse sequence; and
   wherein the XY pulse sequence and the CPMG-n pulse sequence are configured to decouple single NV spins in the ensemble from higher frequency sin-bath fluctuations.

21. The system of claim 19, further comprising an optical source configured to generate optical radiation that prepares the NV centers into $m_s=0$ ground states and drive spin-dependent fluorescence detection from the NV centers, when applied thereto.

22. The system of claim 19, wherein the sources of decoherence in the spin bath environment include fluctuating magnetic fields generated by the $^{13}C$ nuclear spin impurities and N electronic spin impurities, and wherein the magnetic field fluctuations are slow compared to time period between the pulses.

23. The system of claim 21, further comprising a detector configured to detect output optical radiation from the spin impurities after being exposed to the optical excitation signal and the periodic microwave pulses.

24. The system of claim 21, wherein the optical source is a laser tunable to a frequency of about 532 nm.

\* \* \* \* \*